United States Patent
Kuppusamy (10) Patent No.: US 11,865,236 B2
(45) Date of Patent: Jan. 9, 2024

(54) INTRAVENOUS CATHETER DEVICE WITH SLIDING SAFETY MECHANISM

(71) Applicant: Becton, Dickinson and Company, Franklin Lakes, NJ (US)

(72) Inventor: Senthilnathan Kuppusamy, Pin (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 205 days.

(21) Appl. No.: 17/337,238

(22) Filed: Jun. 2, 2021

(65) Prior Publication Data

US 2021/0386976 A1 Dec. 16, 2021

Related U.S. Application Data

(60) Provisional application No. 63/038,569, filed on Jun. 12, 2020.

(51) Int. Cl.
*A61M 5/32* (2006.01)
*A61M 25/06* (2006.01)

(52) U.S. Cl.
CPC ......... *A61M 25/0631* (2013.01); *A61M 5/322* (2013.01); *A61M 5/3243* (2013.01); *A61M 25/0606* (2013.01); *A61M 25/0625* (2013.01); *A61M 2005/3247* (2013.01)

(58) Field of Classification Search
CPC ............ A61M 25/0631; A61M 5/3257; A61M 5/322; A61M 5/3221; A61M 5/326; A61M 5/3234; A61M 5/3243
See application file for complete search history.

(56) References Cited

U.S. PATENT DOCUMENTS

| 5,865,806 | A | * | 2/1999 | Howell | A61M 25/0693 |
| | | | | | 604/164.12 |
| 6,582,402 | B1 | * | 6/2003 | Erskine | A61M 5/3269 |
| | | | | | 604/164.08 |
| 2009/0131872 | A1 | * | 5/2009 | Popov | A61M 25/0631 |
| | | | | | 604/164.08 |
| 2016/0220791 | A1 | | 8/2016 | Akcay et al. | |
| 2019/0314615 | A1 | | 10/2019 | Johnson et al. | |

FOREIGN PATENT DOCUMENTS

EP 0730880 9/1996

OTHER PUBLICATIONS

Becton, Dickinson and Company, BD Insyte™ Autoguard™ BC Shielded IV Catheter with Blood Control Technology, Webpage, <https://www.bd.com/en-us/offerings/capabilities/vascular-access/vascular-iv-catheters/peripheral-iv-catheters/insyte-autoguard-bc-shielded-iv-catheter-with-blood-control-technology> (last accessed Jun. 3, 2021).

* cited by examiner

*Primary Examiner* — Katherine H Schwiker
*Assistant Examiner* — Anna E Goldberg-Richmeier
(74) *Attorney, Agent, or Firm* — Kirton McConkie; Whitney Blair; Kevin Stinger (57) ABSTRACT

An intravenous catheter device can include a safety mechanism having a slider that couples to a catheter adapter and slides relative to a barrel. A needle hub can be contained within the barrel and can be retracted once a catheter has been inserted into the patient's vasculature. The retraction of the needle hub can be triggered by the sliding of the slider. The slider may also function to guard the distal tip of the needle once the needle hub is retracted within the barrel.

19 Claims, 6 Drawing Sheets

INTRAVENOUS CATHETER DEVICE WITH SLIDING SAFETY MECHANISM

RELATED APPLICATIONS

This application claims benefit of U.S. Provisional Patent Application No. 63/038,569, filed on Jun. 12, 2020, entitled INTRAVENOUS CATHETER DEVICE WITH SLIDING SAFETY MECHANISM, which is incorporated herein in its entirety.

BACKGROUND

Intravenous (IV) catheter devices are commonly used for a variety of infusion therapies. For example, an IV catheter device may be used for infusing fluids, such as normal saline solution, various medicaments, and total parenteral nutrition, into a patient. IV catheter devices may also be used for withdrawing blood from the patient.

A common type of IV catheter device is an over-the-needle peripheral intravenous ("IV") catheter ("PIVC"). As its name implies, the over-the-needle catheter may be mounted over a needle having a sharp distal tip. The catheter and the needle may be assembled so that the distal tip of the needle extends beyond the distal tip of the catheter with the bevel of the needle facing up away from skin of the patient. The catheter and needle are generally inserted at a shallow angle through the skin into the vasculature of the patient.

IV catheter devices typically include a safety mechanism for shielding the needle tip after the needle is separated from the catheter. Oftentimes, even with a safety mechanism, the needle tip will be exposed temporarily as it is withdrawn from the catheter and into the safety mechanism. This temporary exposure can lead to blood splatter and enhanced safety risks.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to intravenous catheter devices having a safety mechanism. The safety mechanism can include a slider that couples to a catheter adapter and slides relative to a barrel. A needle hub can be contained within the barrel and can be retracted once a catheter has been inserted into the patient's vasculature. The retraction of the needle hub can be triggered by the sliding of the slider. The slider may also function to guard the distal tip of the needle once the needle hub is retracted within the barrel.

In some embodiments, an intravenous catheter device may include a catheter assembly having a catheter adapter and a catheter that extends distally from the catheter adapter, a needle assembly having a needle hub and a needle that extends distally from the needle hub, the needle extending through the catheter adapter and the catheter, and a safety mechanism having a barrel and a slider that slides within the barrel. A distal end of the slider may be coupled to a proximal end of the catheter adapter such that the catheter assembly slides with the slider relative to the barrel. The needle hub may be contained within the barrel and may be configured to retract proximally within the barrel.

In some embodiments, the slider may include a distal nose that inserts into the catheter adapter to interconnect the safety mechanism and the catheter assembly. In some embodiments, the slider may include a collar that is positioned adjacent to the distal nose. In some embodiments, the collar may form a push tab.

In some embodiments, a position of the needle hub relative to the barrel may remain fixed while the slider initially slides within the barrel. In some embodiments, the needle hub may be retracted proximally within the barrel when the slider slides distally to a trigger point. In some embodiments, the safety mechanism may include a spring that causes the needle hub to retract proximally within the barrel. In some embodiments, the slider may cause the spring to retract the needle hub proximally when the slider reaches the trigger point. In some embodiments, a distal tip of the needle may be retracted into the slider when the needle hub is retracted proximally within the barrel. In some embodiments, a position of the slider relative to the barrel may be retained after the slider reaches the trigger point.

In some embodiments, an intravenous catheter device may include a barrel, a slider that is coupled to and slides within the barrel, a catheter adapter having a proximal end to which a distal end of the slider is coupled, a catheter that extends distally from the catheter adapter, a needle hub contained within the barrel and a needle that extends distally from the needle hub. The needle extends through the catheter adapter and the catheter.

In some embodiments, the needle hub may initially be positioned towards a distal end of the barrel. In some embodiments, the needle hub may be retained towards the distal end of the barrel while the slider slides towards a trigger point. In some embodiments, the needle hub may be retracted to a proximal end of the barrel when the slider reaches the trigger point. In some embodiments, the intravenous catheter device may include a spring that is compressed when the needle hub is retained towards the distal end of the barrel. The spring may force the needle hub to retract to the proximal end of the barrel in response to the slider reaching the trigger point.

In some embodiments, a distal tip of the needle may be contained within the slider when the needle hub is retracted to the proximal end of the barrel. In some embodiments, the slider may be retained at the trigger point to prevent the distal tip of the needle from extending distally beyond the slider. In some embodiments, the slider may include a push tab. In some embodiments, the slider may include a distal nose that inserts into the catheter adapter to couple the slider to the catheter adapter.

In some embodiments, an intravenous catheter device may include a barrel having an interior, a slider contained in the interior of the barrel, a catheter adapter having a proximal end to which a distal end of the slider is coupled, a catheter that extends distally from the catheter adapter, a needle hub contained within the interior of the barrel and a needle that extends distally from the needle hub with the needle extending through the catheter adapter and the catheter. A proximal end of the slider may initially be positioned towards a proximal end of the barrel and the needle hub may initially be retained towards a distal end of the barrel. The needle hub may be retracted to the proximal end of the barrel when the proximal end of the slider is slid to a trigger point of the barrel. The retracting of the needle hub may cause a distal tip of the needle to be secured within the slider.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

An IV catheter device that is suitable for embodiments of the present disclosure may typically include a catheter assembly, a needle assembly and a safety mechanism that are initially interconnected. After insertion of the catheter into the patient's vasculature, the needle assembly of such IV catheter devices is typically withdrawn into the safety mechanism as part of detaching the needle assembly from the catheter assembly. In embodiments of the present disclosure, the safety mechanism of such IV catheter devices can be configured to slide to enhance the safety and simplify the use of the IV catheter devices.

Figure 1:
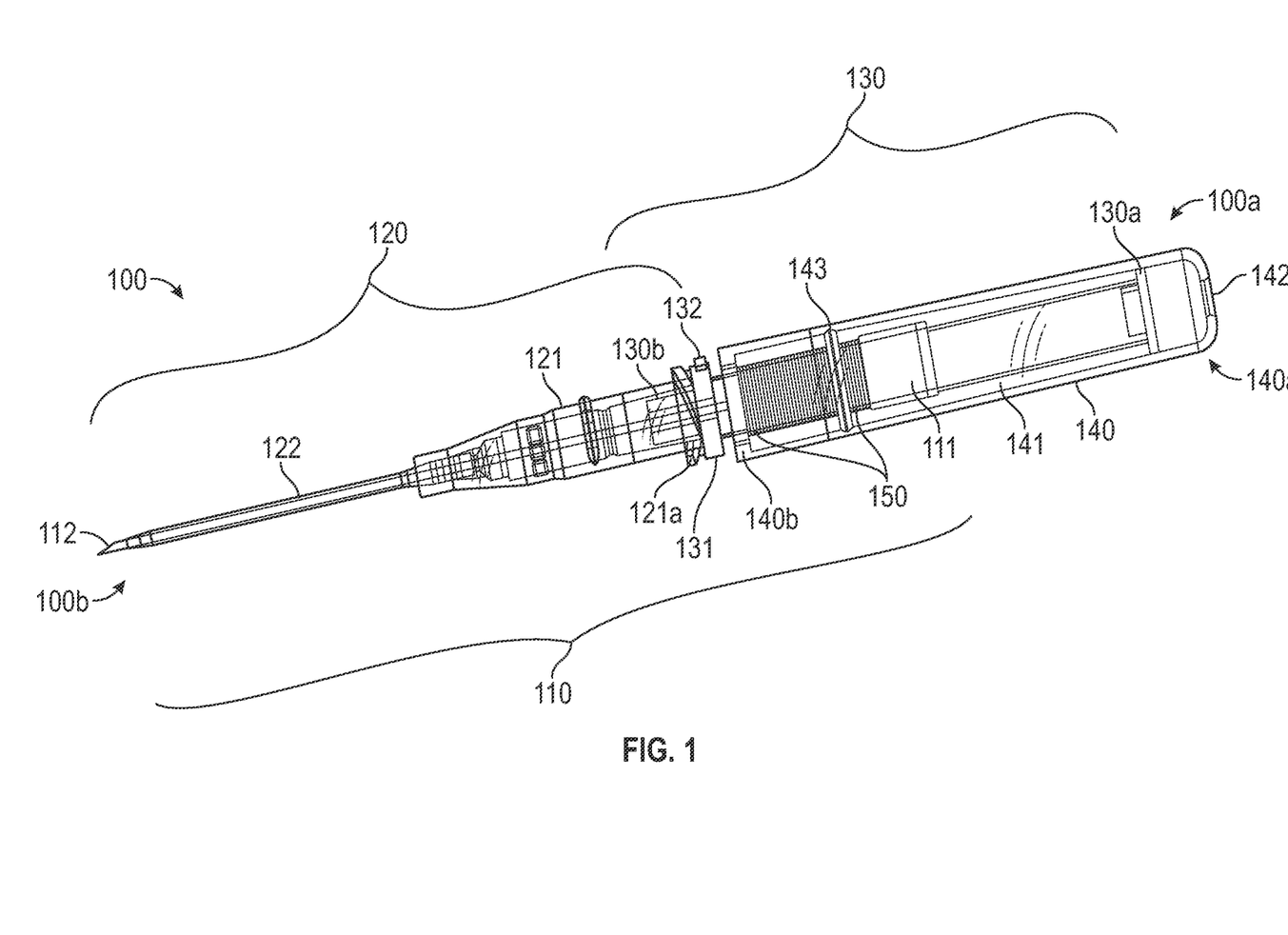
FIG. 1 illustrates an example of an IV catheter device with a safety mechanism that includes a slider in accordance with some embodiments.

FIGS. 1-5 illustrate an example of an IV catheter device 100 that is configured in accordance with some embodiments. FIG. 1 illustrates IV catheter device 100 in a pre-insertion configuration. For example, IV catheter device 100 could be in this pre-insertion configuration when the clinician unpackages it and/or prior to the clinician inserting the needle through the patient's skin. IV catheter device 100 includes a needle assembly 110, a catheter assembly 120 and a safety mechanism 190. Needle assembly 110 includes a needle hub 111 and a needle 112 that extends distally from needle hub 111 to distal end 100b of IV catheter device 100. Catheter assembly 120 includes a catheter adapter 121 and a catheter 122 that extends distally from catheter adapter 121.

Safety mechanism 190 includes a slider 130 and a barrel 140 with respect to which slider 130 slides. A proximal end 140a of barrel 140 is positioned at proximal end 100a of IV catheter device 100. In the pre-insertion configuration, a distal end 140b of barrel 140 is positioned towards proximal end 121a of catheter adapter 121, while a proximal end 130a of slider 130 is positioned towards proximal end 140a of barrel 140. A distal nose 130b of slider 130 inserts into catheter adapter 121 and may form a friction fit to maintain the interconnection between safety mechanism 190 and catheter assembly 120. Slider 130 also includes a collar 131 that is positioned towards distal nose 130b. Collar 131 may be adjacent to or abut proximal end 121a of catheter adapter 121 when distal nose 103b is inserted into catheter adapter 121. Accordingly, in the pre-insertion configuration, slider 130 is coupled to catheter adapter 121 and may be inserted fully into barrel 140.

In the pre-insertion configuration, needle hub 111 may also be positioned within interior 141 of barrel 140 but spaced distally from proximal end 140a of barrel 140. A length of needle assembly 110 can be configured to cause the distal tip of needle 112 to extend distally beyond catheter 122. A spring 150 can be positioned within interior 141 and can be compressed between needle hub 111 and distal end 140b of barrel 140. Interior 141 and needle hub 111 can be configured to form an interference fit that retains needle hub 111 in the depicted position even though spring 150 is applying a proximally-directed force against needle hub 111. For example, a trigger point 143 in the form of a groove or other recessed portion in the sidewall of interior 141 may receive an outwardly-biased portion (not shown) of needle hub 111 to lock the position of needle hub 111. Accordingly, in the pre-insertion configuration, needle hub 111 is spaced from but may be biased towards proximal end 140a of barrel 140. In some embodiments, an interference fit may be formed between spring 150 and barrel 140 rather than between needle hub 111 and barrel 140. For example, a proximal end of spring 150 may be interfaced with trigger point 143 to maintain the compressed state of spring 150.

In some embodiments, barrel 140 can include a vent plug 142 (e.g., at proximal end 140a) that is configured to vent air from within interior 141. Vent plug 142 can therefore facilitate blood flashback through needle 112 and possibly into interior 141. In some embodiments, a seal (not labelled) may be formed between slider 130 and the opening in distal end 140b of barrel 140 to prevent blood or other fluid from escaping from within interior 141.

Figure 2:
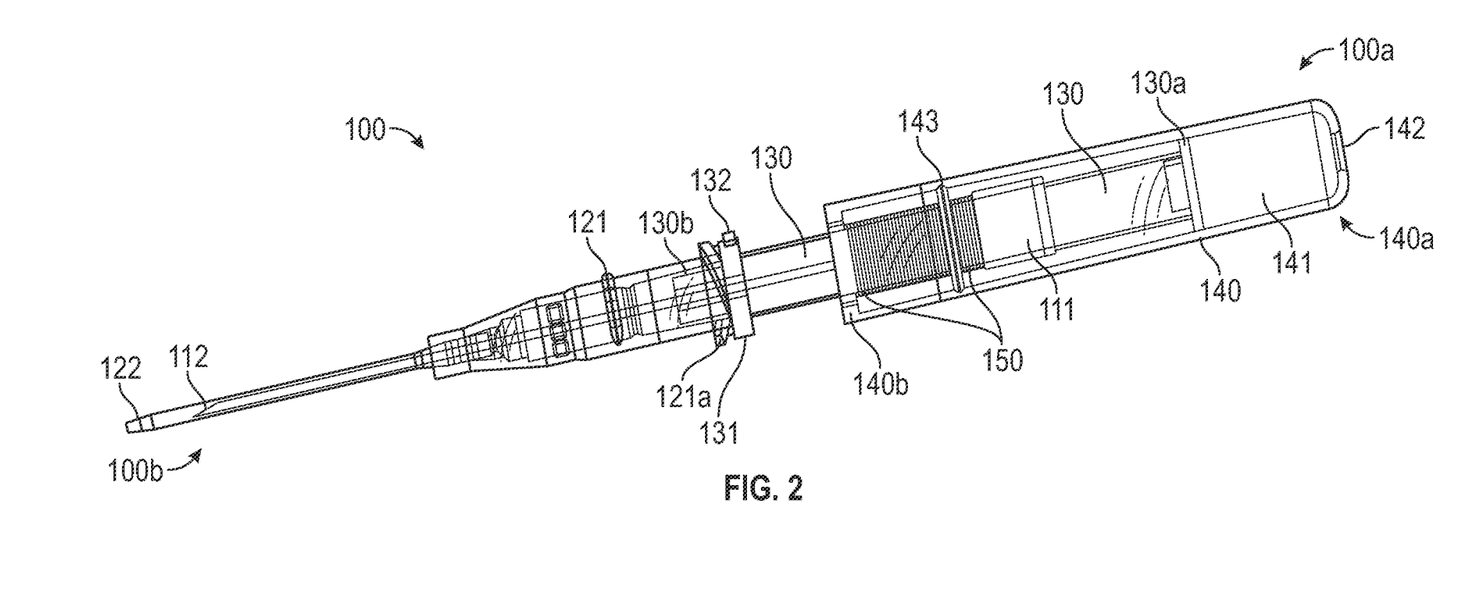
FIG. 2 illustrates the IV catheter device of FIG. 1 when the slider has been slid partially out from a barrel of the safety mechanism in accordance with some embodiments.

Turning to FIG. 2, IV catheter device 100 is now depicted after slider 130 has been slid distally relative to barrel 140. Because slider 130 is coupled to catheter adapter 121, the sliding of slider 130 relative to barrel 140 causes catheter 122 to slide relative to needle 112. For example, after the clinician inserts the distal tip of the needle into the patient's vasculature, he or she may apply a distal force to push tab 132 on collar 131 while retaining the position of barrel 140 (or slightly withdrawing barrel 140) to thereby advance catheter 122 overtop of needle 112 and further into the patient's vasculature. The relative position of needle hub 111 within barrel 140 remains fixed at this point. Accordingly, the movement of slider 130 causes proximal end 130a of slider 130 to approach needle hub 111.

Figure 3:
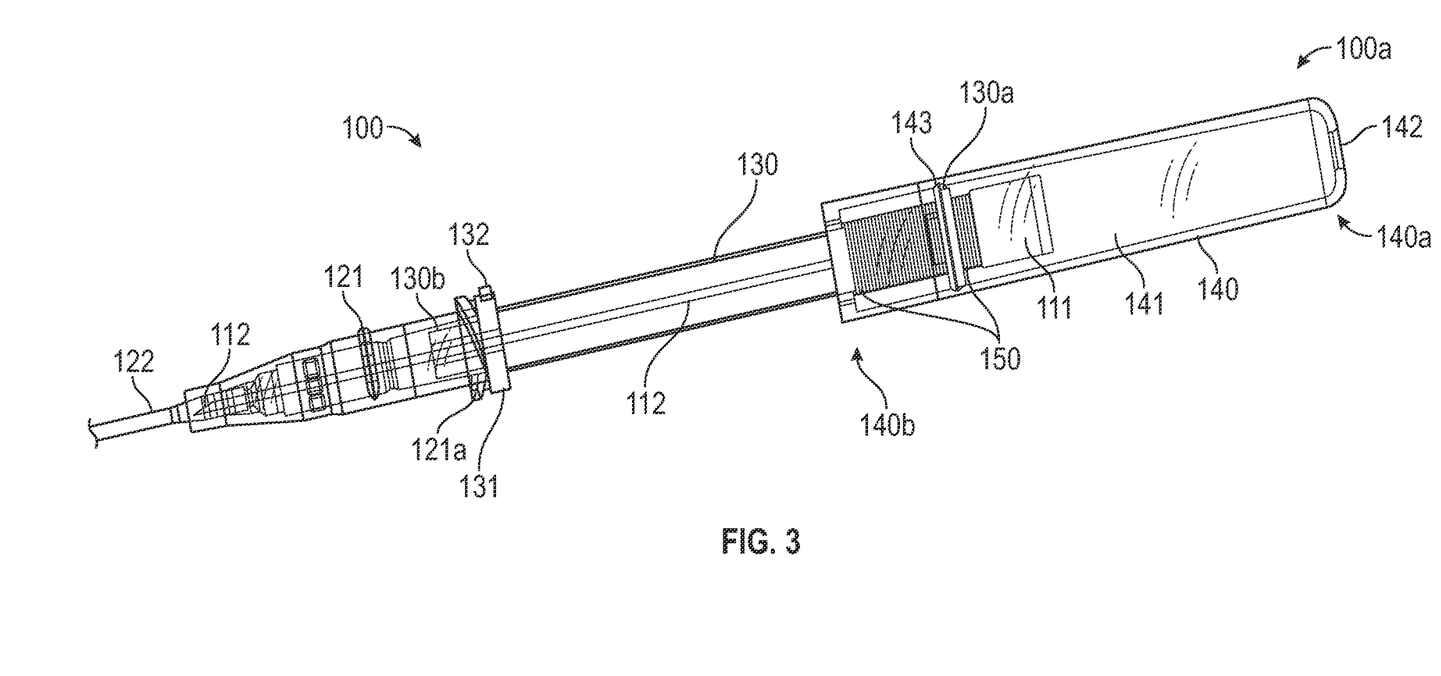
FIG. 3 illustrates the IV catheter device of FIG. 1 when the slider has been slid to a trigger point in accordance with some embodiments.

Turning to FIG. 3, IV catheter device 100 is now depicted after slider 130 has been slid distally relative to barrel 140 to the point that proximal end 130a of slider 130 has reached trigger point 143. At this point, catheter 122 will have been advanced substantially beyond the distal tip of needle 112, and the clinician may likely have withdrawn barrel 140 sufficiently to remove the distal tip of needle 112 from the patient's vasculature. For example, in some embodiments, IV catheter device 100 may be designed to cause the distal tip of needle 112 to be positioned at least partially within catheter adapter 121 (i.e., outside the vasculature) when proximal end 130a of slider 130 reaches trigger point 143.

For illustrative purposes, FIG. 3 shows that needle hub 111 is still being held in position. However, in some embodiments, needle hub 111 may be released from its interference fit substantially simultaneous with the arrival of proximal end 130a of slider 130 at trigger point 143.

Figure 4:
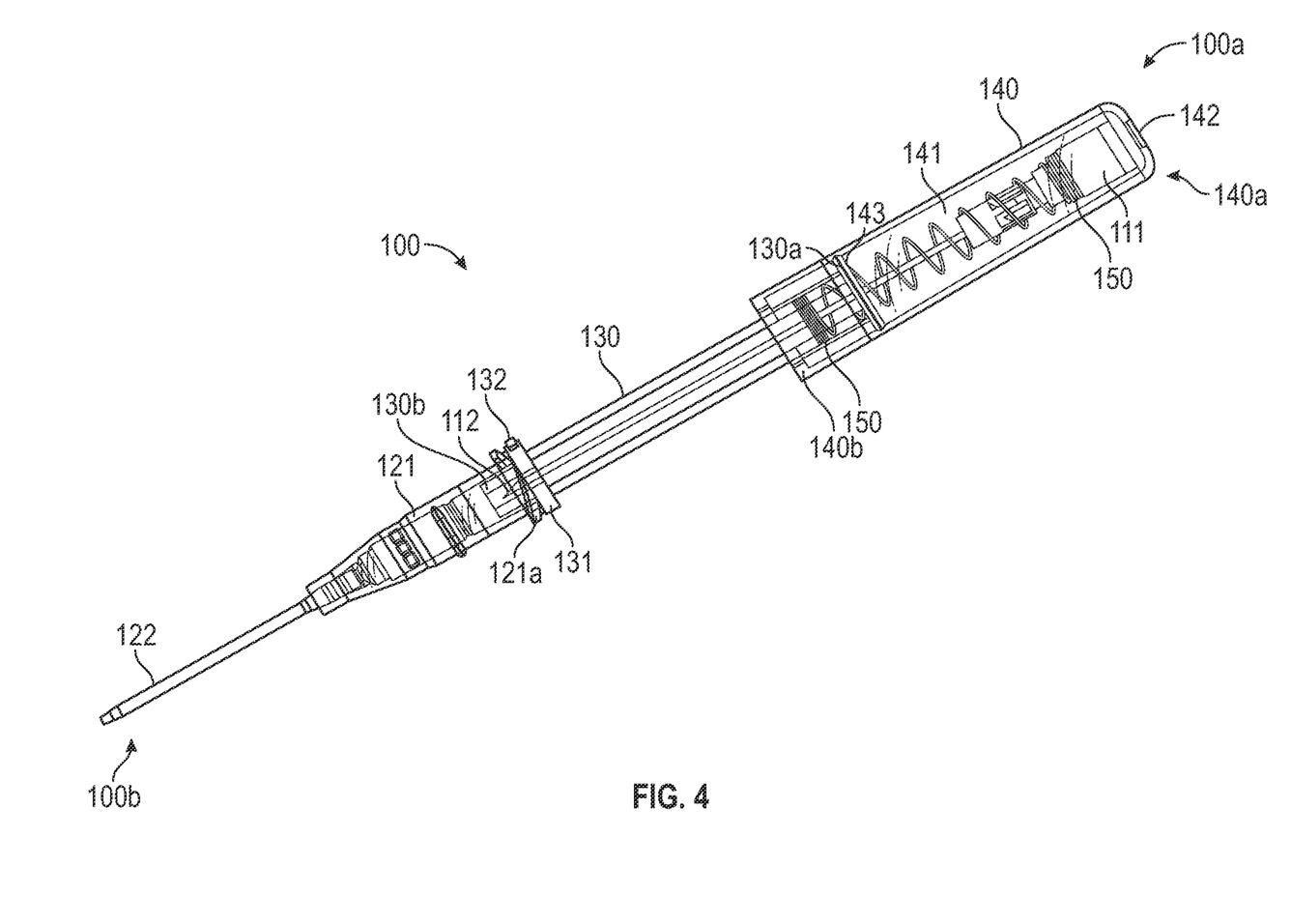
FIG. 4 illustrates the IV catheter device of FIG. 1 after the needle has been retracted into the slider in accordance with some embodiments.

Turning to FIG. 4, needle assembly 110 is depicted as having been withdrawn fully into barrel 140. In particular, as the interference fit between needle hub 111 (or spring 150) and barrel 140 is released in response to the sliding of slider 130, spring 150 forces needle hub 111 to proximal end 140a of barrel 140 thereby withdrawing the distal tip of needle 112 into slider 130. For example, in FIG. 4, the distal tip of needle 112 is contained within distal nose 130b of slider 130 once needle hub 111 is positioned at proximal end 140a so that the distal tip of needle 112 will not be exposed once slider 130 is detached from catheter adapter 121. In some embodiments, proximal end 130a of slider 130 may be configured to release the interference fit between needle hub 111 and barrel 140. For example, if the interference fit is formed by inserting a portion of needle hub 111 into trigger point 143, the distal movement of proximal end 130a of slider 130 may cause the portion of needle hub 111 to be removed from trigger point 143.

As stated above, in some embodiments, slider 130 may be coupled to catheter adapter 121 only by the frictional force between distal nose 130b and the interior walls of catheter adapter 121. In such cases, slider 130 can be detached from catheter adapter 121 by pulling (and possibly twisting) slider 130 relative to catheter adapter 121. In contrast, in some embodiments, collar 131 and/or distal nose 130b may be coupled to proximal end 121a of catheter adapter 121 in a way that prevents slider 130 from separating from catheter adapter 121 until after the distal tip of needle 112 has been withdrawn into slider 130. For example, catheter adapter 121 may be configured to be threaded onto slider 130. In such cases, the structure of catheter adapter 121 and slider 130 may be configured to prevent rotation of slider 130 relative to catheter adapter 121 until after the distal tip of needle 112 has passed into slider 130. For example, needle 112 may include a feature that enables this relative rotation only when the feature is positioned inside distal nose 130b and/or collar 131. In some embodiments, this feature could be in the form of a notch in needle 112 that allows a component (not shown) that would otherwise block the relative rotation to be slid annularly inwardly into the notch, which in turn will enable slider 130 to be rotated off of catheter adapter 121. In some embodiments, this feature could be in the form of a protrusion in needle 112 that forces a component (not shown) that would otherwise block the relative rotation to be slid annularly outwardly, which in turn will enable slider 130 to be rotated off of catheter adapter 121.

Figure 5:
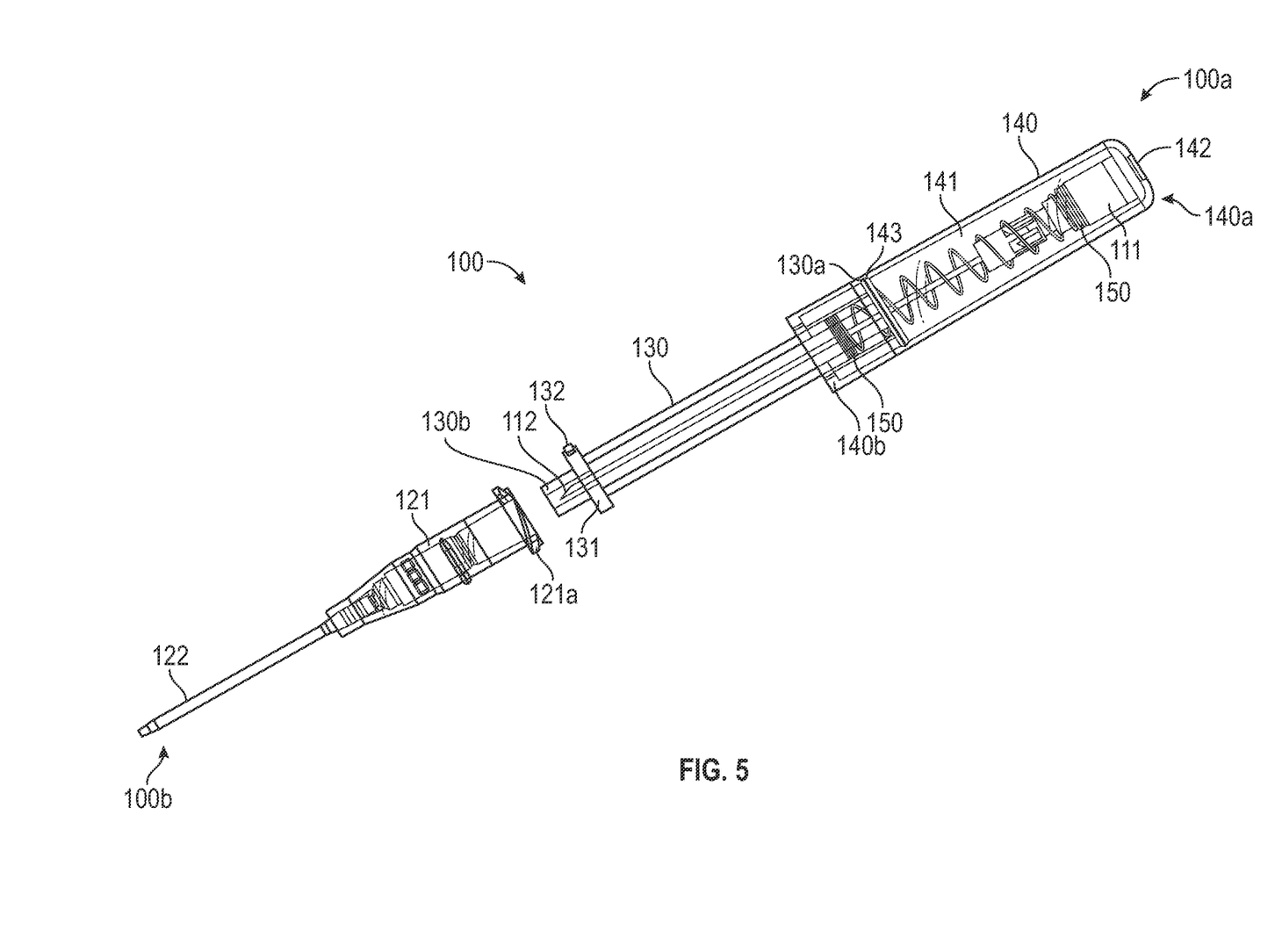
FIG. 5 illustrates the IV catheter device of FIG. 1 after the safety mechanism has been detached from the catheter assembly in accordance with some embodiments.

In any case, once the distal tip of needle 112 is secured within slider 130, the clinician may detach slider 130 from catheter adapter 121 as shown in FIG. 5. Proximal end 130a of slider 130 and trigger point 143 can be configured to form an interference fit that prevents slider 130 from sliding proximally relative to barrel 140. This interference fit can ensure that the distal tip of needle 112 remains secured within slider 130 once slider 130 has been detached from catheter adapter 121.

Figure 6:
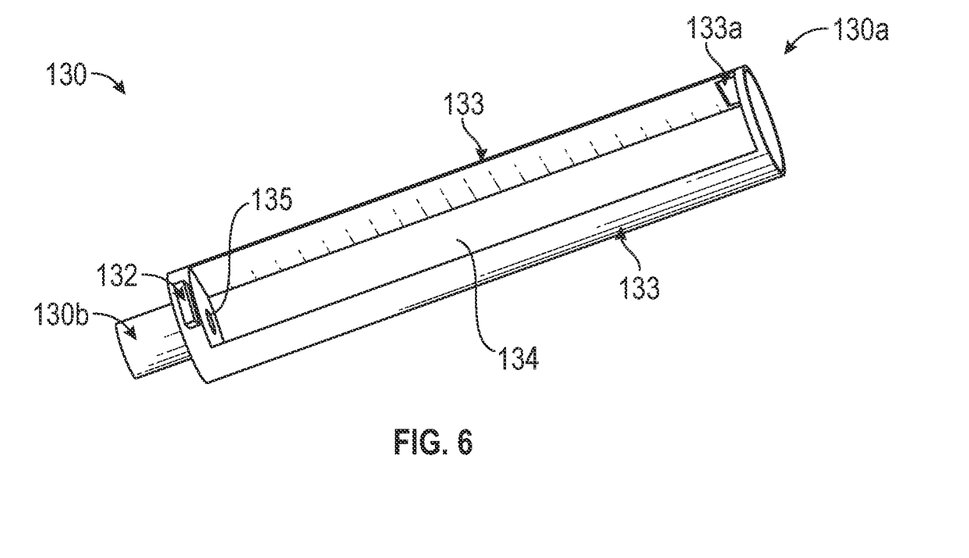
FIG. 6 provides an isolated view of an example of a slider that is configured in accordance with some embodiments.

FIG. 6 provides an isolated view of slider 130 as it may be configured in some embodiments. As shown, slider 130 may include sidewalls 133 and one or more openings 134 that extend between proximal end 130a and distal nose 130b. The use of openings 134 can reduce the amount of material required to form slider 130. A tab 133a can be formed on one or more of sidewalls 133 towards proximal end 130a. In some embodiments, tab 133a can form an interference fit with trigger point 143 to prevent slider 130 from sliding proximally within barrel 140 after the distal tip of needle 112 has been withdrawn into distal nose 130b. A needle channel 135 is formed through distal nose 130b. In some embodiments, needle channel 135 may have a diameter that is slightly larger than the diameter of needle 112 to thereby act as a support for preventing excessive vibration of needle 112 as it is withdrawn into barrel 140 and slider 130.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

I claim:
1. An intravenous catheter device comprising:
a catheter assembly having a catheter adapter and a catheter that extends distally from the catheter adapter;
a needle assembly having a needle hub and a needle that extends distally from the needle hub, the needle extending through the catheter adapter and the catheter; and
a safety mechanism having a barrel and a slider that slides within the barrel, a distal end of the slider being coupled to a proximal end of the catheter adapter such that the catheter assembly slides with the slider relative to the barrel, the needle hub being contained within the barrel and being configured to retract proximally within the barrel, wherein the needle hub is retracted proximally within the barrel when the slider slides distally to a trigger point, wherein a proximal end of the slider is configured to form an interference fit with the trigger point to prevent the slider from sliding proximally relative to the barrel.
2. The intravenous catheter device of claim 1, wherein the slider includes a distal nose that inserts into the catheter adapter to interconnect the safety mechanism and the catheter assembly.
3. The intravenous catheter device of claim 2, wherein the slider includes a collar that is positioned adjacent to the distal nose.
4. The intravenous catheter device of claim 3, wherein the collar forms a push tab.
5. The intravenous catheter device of claim 1, wherein a position of the needle hub relative to the barrel remains fixed while the slider initially slides within the barrel.
6. The intravenous catheter device of claim 5, wherein the safety mechanism includes a spring that causes the needle hub to retract proximally within the barrel.
7. The intravenous catheter device of claim 6, wherein the slider causes the spring to retract the needle hub proximally when the slider reaches the trigger point.
8. The intravenous catheter device of claim 7, wherein a distal tip of the needle is retracted into the slider when the needle hub is retracted proximally within the barrel.
9. The intravenous catheter device of claim 8, wherein a position of the slider relative to the barrel is retained after the slider reaches the trigger point.
10. An intravenous catheter device comprising:
a barrel;
a slider that is coupled to and slides within the barrel;

a catheter adapter having a proximal end to which a distal end of the slider is coupled;
a catheter that extends distally from the catheter adapter;
a needle hub contained within the barrel; and
a needle that extends distally from the needle hub, the needle extending through the catheter adapter and the catheter, wherein the needle hub is retracted proximally within the barrel when the slider slides distally to a trigger point, wherein a proximal end of the slider is configured to form an interference fit with the trigger point to prevent the slider from sliding proximally relative to the barrel.

11. The intravenous catheter device of claim 10, wherein the needle hub is initially positioned towards a distal end of the barrel.

12. The intravenous catheter device of claim 11, wherein the needle hub is retained towards the distal end of the barrel while the slider slides towards the trigger point.

13. The intravenous catheter device of claim 12, wherein the needle hub is retracted to a proximal end of the barrel when the slider reaches the trigger point.

14. The intravenous catheter device of claim 13, further comprising:
a spring that is compressed when the needle hub is retained towards the distal end of the barrel, the spring forcing the needle hub to retract to the proximal end of the barrel in response to the slider reaching the trigger point.

15. The intravenous catheter device of claim 13, wherein a distal tip of the needle is contained within the slider when the needle hub is retracted to the proximal end of the barrel.

16. The intravenous catheter device of claim 15, wherein the slider is retained at the trigger point to prevent the distal tip of the needle from extending distally beyond the slider.

17. The intravenous catheter device of claim 10, wherein the slider includes a push tab.

18. The intravenous catheter device of claim 10, wherein the slider includes a distal nose that inserts into the catheter adapter to couple the slider to the catheter adapter.

19. An intravenous catheter device comprising:
a barrel having an interior;
a slider contained in the interior of the barrel;
a catheter adapter having a proximal end to which a distal end of the slider is coupled;
a catheter that extends distally from the catheter adapter;
a needle hub contained within the interior of the barrel; and
a needle that extends distally from the needle hub, the needle extending through the catheter adapter and the catheter;
wherein a proximal end of the slider is initially positioned towards a proximal end of the barrel and the needle hub is initially retained towards a distal end of the barrel; and
wherein the needle hub is retracted proximally within the barrel when the slider slides distally to a trigger point, the retracting of the needle hub causing a distal tip of the needle to be secured within the slider, wherein the proximal end of the slider is configured to form an interference fit with the trigger point to prevent the slider from sliding proximally relative to the barrel.

\* \* \* \* \*